United States Patent [19]

Termanini

[11] 4,159,544
[45] Jul. 3, 1979

[54] HIP JOINT PROSTHESIS
[75] Inventor: Zafer A. Termanini, Brooklyn, N.Y.
[73] Assignee: Zafmedico Corporation, Brooklyn, N.Y.
[21] Appl. No.: 855,336
[22] Filed: Nov. 28, 1977
[51] Int. Cl.² .................................................. A61F 1/24
[52] U.S. Cl. .................................... 3/1.912; 128/92 C
[58] Field of Search ................... 3/1.912, 1.913, 1.91, 3/1.9; 128/92 C, 92 CA

[56] References Cited
U.S. PATENT DOCUMENTS

| 2,947,308 | 8/1960 | Gorman | 3/1.912 X |
| 3,818,512 | 6/1974 | Shersher | 3/1.912 |
| 3,875,593 | 4/1975 | Shersher | 3/1.912 |

FOREIGN PATENT DOCUMENTS 1260046  1/1972  United Kingdom ................... 3/1.912

Primary Examiner—Ronald L. Frinks
Attorney, Agent, or Firm—Fitzpatrick, Cella, Harper & Scinto

[57] ABSTRACT

A hip joint prosthesis including a cup-shaped socket member for being implanted in an acetabular opening, and a ball-shaped member having a shaft attached thereto for being implanted in a femoral opening, wherein after implantation of the socket and ball members, the two members are assembled together for relative movement, and locked in place by an adjustable mechanism. The adjustable mechanism is coupled to the cup-shaped member by springs, wherein forces tending to separate the ball from the socket will be partially absorbed by the springs, thus reducing the likelihood that the cup-shaped member will become dislodged from the acetabular opening.

8 Claims, 11 Drawing Figures

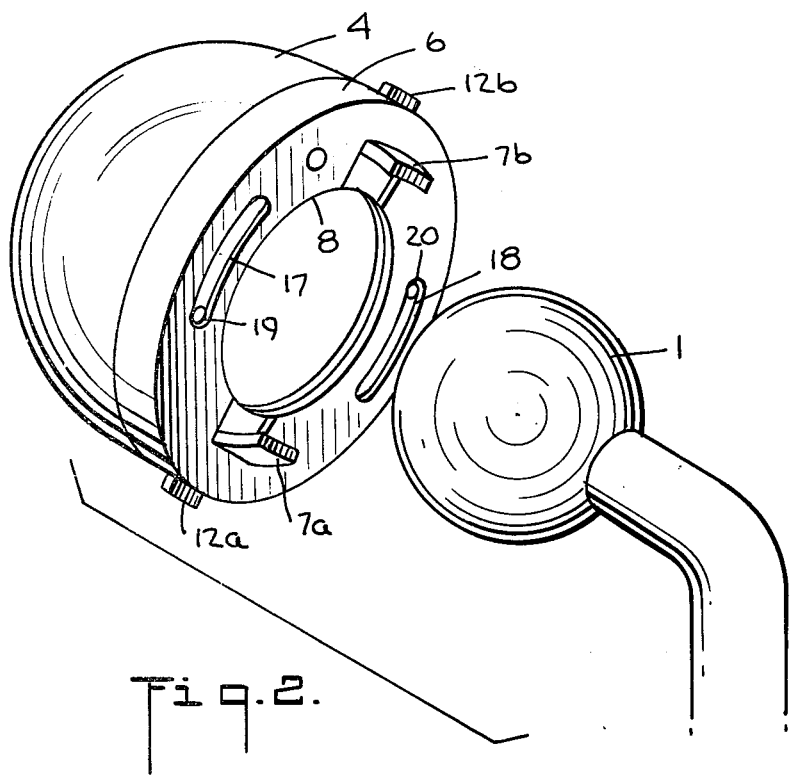
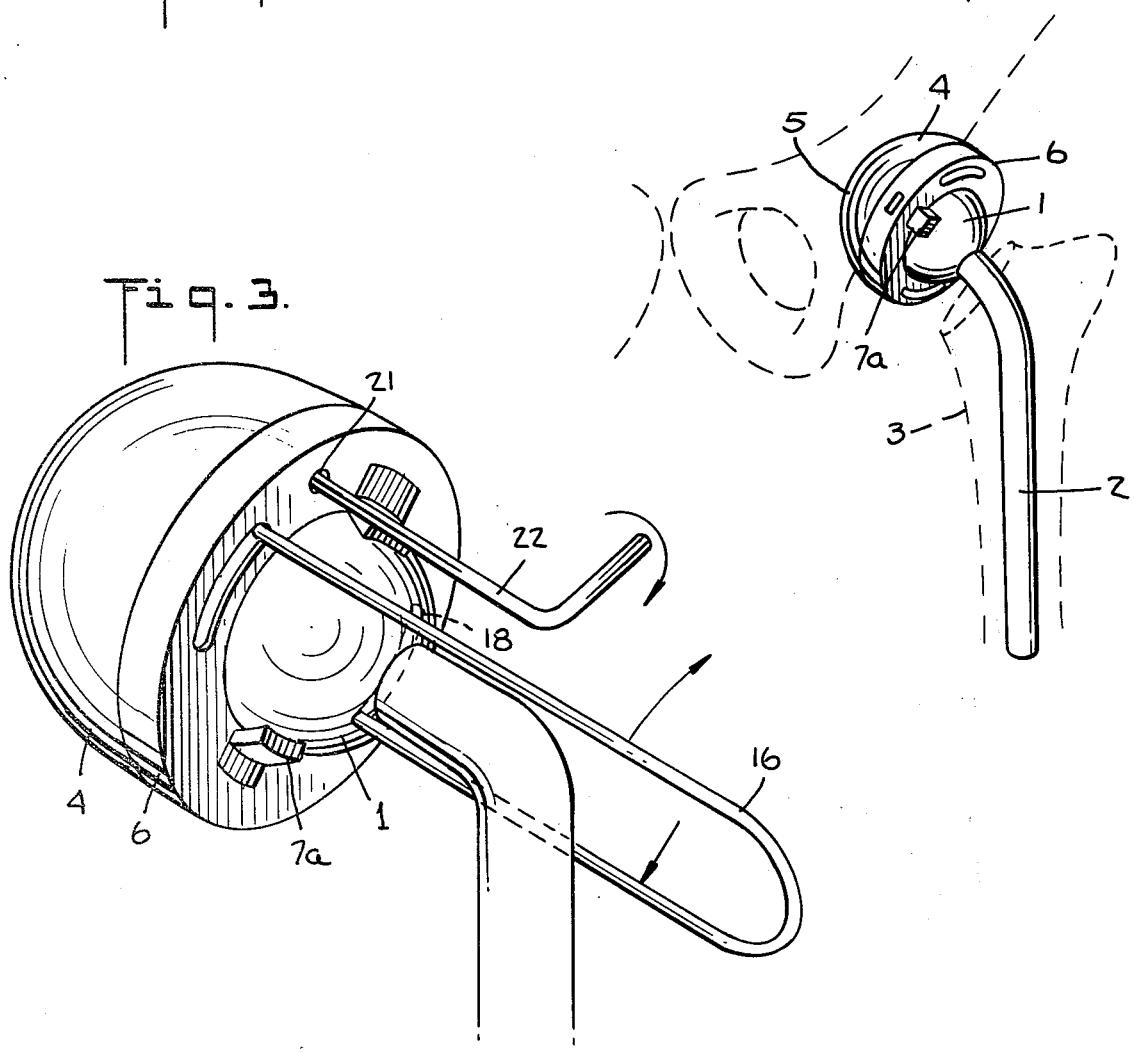

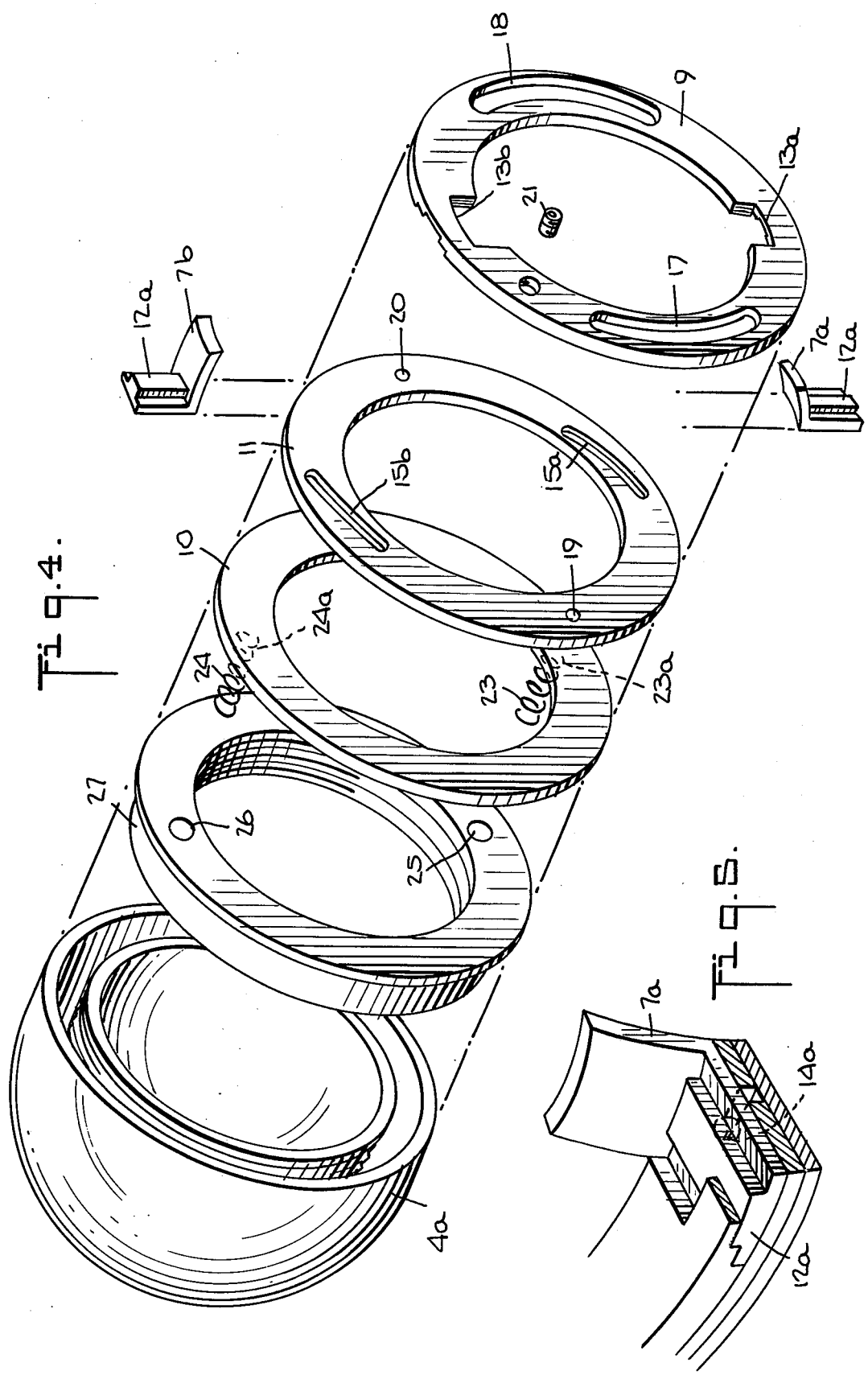

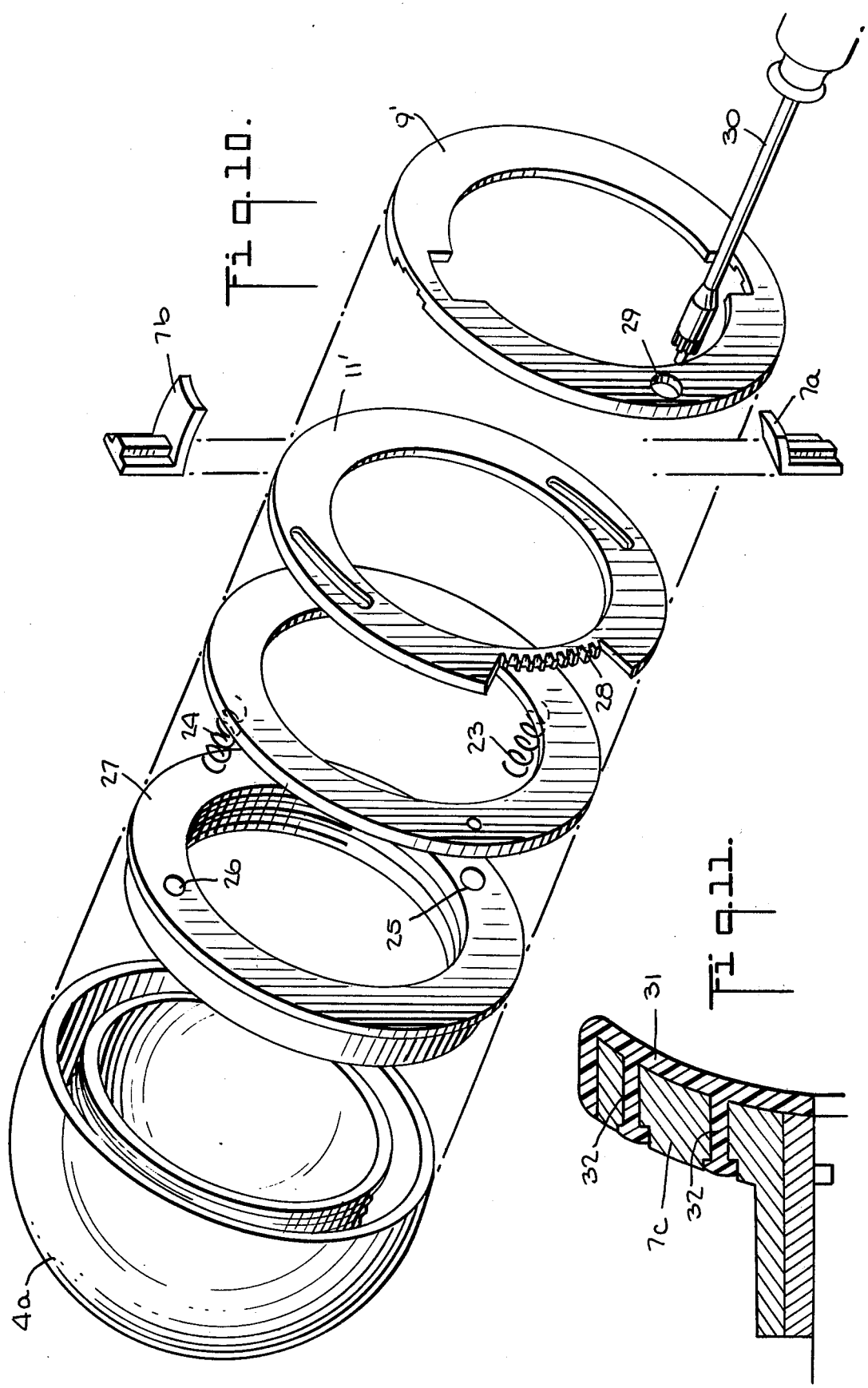

HIP JOINT PROSTHESIS

BACKGROUND OF THE INVENTION

Several types of artificial hip joint devices are available for use by surgeons, and such devices usually take one of two forms; namely, a pre-assembled ball and socket device, or a device wherein the ball and socket members are implanted separately whereupon the ball element is forced into a resilient opening in the socket and thereafter held in place by the resilient material. In the case of the pre-assembled elements, several undesirable effects have been encountered, in that it is sometimes very difficult to manipulate the patient's prosthesis-receiving openings into the precise alignment required to receive the outer portion of the socket member, and the stem which extends from the ball element. Furthermore, it is difficult to maintain such alignment during the curing of cement utilized to hold the elements in place. Also, in the case of presently known pre-assembled prostheses, ambulatory motions of the patient, especially during early recuperative periods, sometimes cause the socket element to be dislodged from the acetabular opening, since the joining force between the socket and the opening constitutes the "weak-link" of the prosthesis.

In the case of socket elements having a resilient retaining ring, for allowing the ball member to be forceably inserted into the socket after the two elements are implanted, the resilient member, by its very nature, constitutes the weak-link so that the forces exerted on the prosthesis by ambulatory motion may cause the ball to be separated from the socket, and such force is generally required to be no greater than the force required to be exerted by the surgeon to insert the ball into the socket. In any event, separation of the ball and socket, or the dislodging of the socket element from the acetabular opening, both require the patient to be subjected to another operation to remedy the prosthesis failure. Accordingly, it is a principal object of the present invention to overcome the above-described deficiencies of prior known devices.

SUMMARY OF THE INVENTION

In accordance with the present invention, separate ball and socket members are provided to be implanted during an operation for installing a hip joint prosthesis. As is common in such operations, an opening is formed in the upper end of the patient's femur, and the ball member is provided with a shaft for being inserted in the pre-formed opening. Also, the socket member is cemented in an acetabular opening constructed by the surgeon. The socket member embodies a retaining mechanism which may be adjusted, after the installation of each of the elements and after the ball has been inserted in the socket, in a manner wherein the assembled ball and socket are fixed in place and cannot be separated no matter how great a force may be later applied to the prosthesis joint due to ambulatory movements of the patient.

Furthermore, to reduce the likelihood that the socket member may become dislodged from its cemented disposition in the acetabular opening, the retaining mechanism, which holds the ball in place within the socket, is mounted to the cemented portion of the socket by springs. For example, a plurality of coil springs may be distributed around the periphery of the socket, and connected as described, whereupon forces tending to separate the socket from the acetabular opening will be absorbed by the springs thereby strengthening the weakest portion of the prosthesis.

BRIEF DESCRIPTION OF THE DRAWINGS

Preferred embodiments of the invention will be described in detail in conjunction with the accompanying drawings, in which:

FIG. 1 is a pictorial view illustrating a preferred embodiment of a hip joint prosthesis after the elements thereof have been implanted and assembled to form a complete hip joint;

FIG. 2 illustrates the ball and socket elements, of the prosthesis of FIG. 1, prior to their assembly;

FIG. 3 shows the ball member received within the socket, and illustrates the use of tools for operating an adjustable mechanism of the socket member for retaining and locking the ball and socket members together;

FIG. 4 is an exploded view illustrating the socket member, and the adjustable retaining mechanism which forms a part thereof;

FIGS. 5, 6 and 7 are enlarged views showing the operation of the retaining mechanism;

FIG. 10 is an exploded view illustrating a modified locking mechanism; and

FIG. 11 is an enlarged view of an arcuate flange which forms a part of the adjustable retaining mechanism of the socket member for engaging the ball member to hold it in an assembled condition, wherein the ball engaging surface of the flange is coated with a frictionless material.

DETAILED DESCRIPTION OF THE PREFERRED EMBODIMENTS

Figure 6:
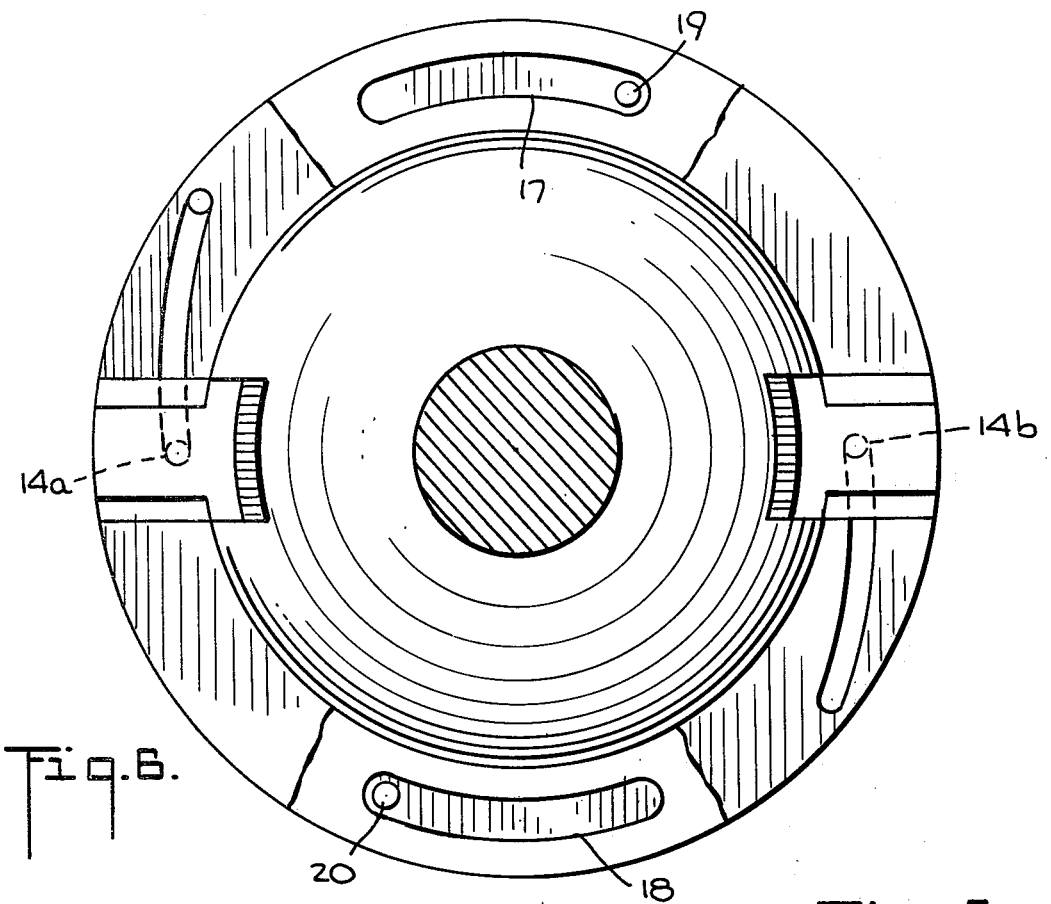

The present invention relates to a hip joint prosthesis as depicted in FIG. 1, embodying a ball element 1 having a shaft 2 fixed thereto for reception in an opening at the upper end 3 of a patient's femur. During installation of the prosthesis, and after the requisite femoral opening is provided, the shaft 2 is inserted in the femur and cemented in place. Conventionally, socket member 4 is implanted in a surgically formed acetabular opening 5 by being cemented in place. In accordance with the present invention, an adjustable locking mechanism 6 is provided on the socket member 4 so that the separately implanted ball element 1 and socket element 4 may be assembled together for relative movement, and locked in place to prevent any inadvertent subsequent separation of the two elements.

Prior to inserting the ball member 1 into the socket 4, the adjustable locking mechanism 6 is opened so that a pair of diametrically opposed arcuate flange members 7a and 7b are spaced apart to a maximum degree, as illustrated in FIG. 2, whereupon the ball 1 may be received into the socket member 4 through an opening 8 in the locking mechanism 6. When the ball and socket members have been assembled, the locking mechanism is adjusted, as shown in FIG. 3, to move the arcuate flange members 7a,7b toward the ball 1, so that when the mechanism is closed the flange members operate to restrain the ball from being removed from its assembled position within the socket member 4.

Figure 7:
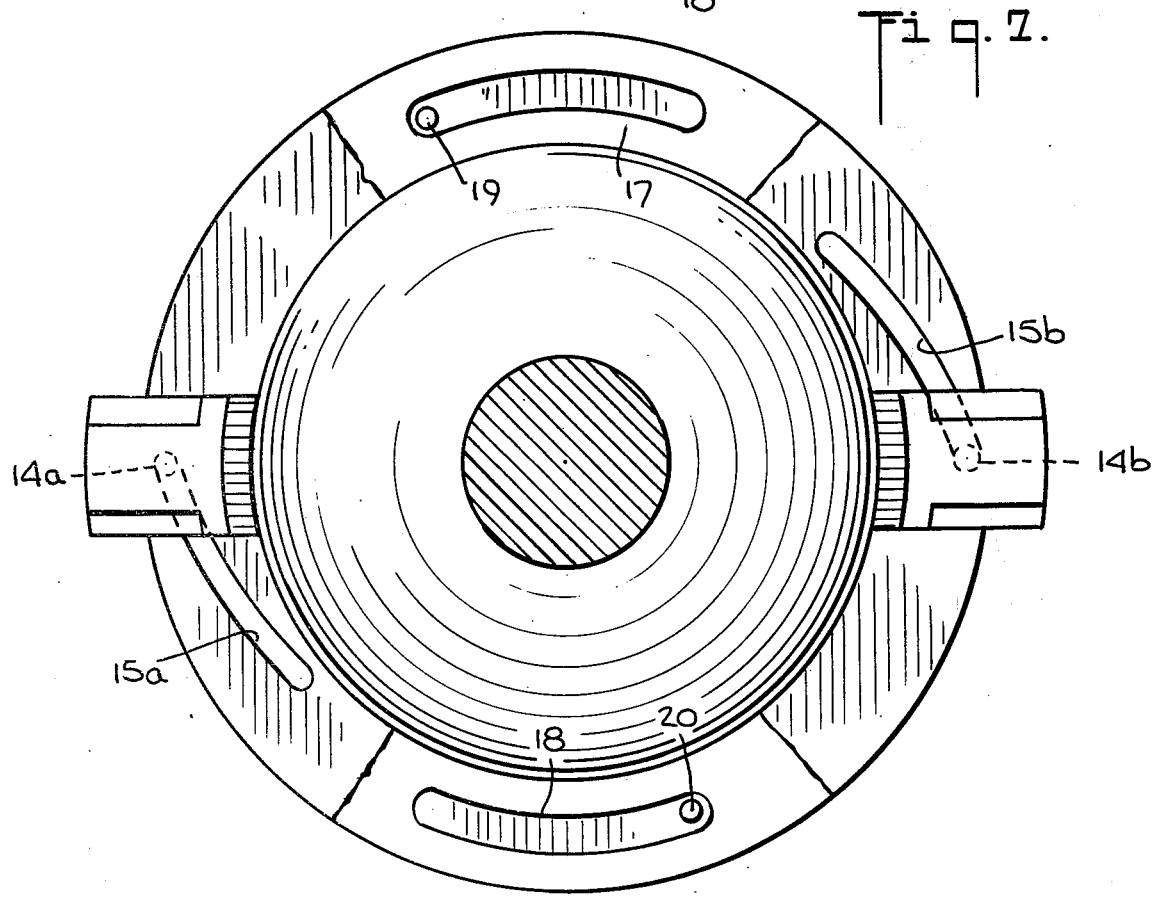

In the embodiment of the invention illustrated particularly in FIGS. 2-7, the locking mechanism 6 includes outer and inner rings 9 and 10, such rings being fixed together and having an intermediate ring 11 disposed axially and rotatably therebetween. Each of the arcuate flanges 7a,7b has a contoured slide element 12a,12b extending radially therefrom for movement within a correspondingly contoured respective slot 13a,13b in the outer ring 9. Furthermore, each of the slide elements is provided with a depending pin 14a,14b which projects into a respective camming groove 15a,15b in the intermediate ring 11. Each of the camming grooves extends semi-circumferentially, from a position close to the opening 8 in the intermediate ring toward the outer periphery thereof. Accordingly, it will be appreciated that as the intermediate ring 11 is rotated, the engagement between the camming grooves 15a,15b and the depending pins 14a,14b will exert a camming force on the pins, thus causing the slide elements 12a,12b to move radially within the slots 13a,13b in the outer ring 9. Such rotation of the intermediate ring may be effected, for example, by a wire tool 16 as illustrated in FIG. 3, wherein slots 17,18 are cut through the outer ring 9 to provide access to depressions 19,20 in the intermediate ring, and wherein the ends of the U-shaped wire tool 16 are received in the depressions 19,20, whereupon a torque may be applied to rotate the intermediate ring 11 in either a clockwise or counterclockwise direction. As depicted in FIGS. 3 and 6, a clockwise rotation of the intermediate ring 11 causes the arcuate flanges 7a,7b to move inward, while as shown in FIGS. 2 and 7, a counterclockwise rotation of the intermediate ring will cause the pins 14a,14b on the slides 12a,12b to be cammed outwardly, thereby opening the arcuate flange members 7a,7b to permit the ball member 1 to be inserted into the socket 4. As also shown in FIG. 3, when the ball and socket have been assembled, and when the intermediate ring has been rotated clockwise to bring the arcuate flanges into locking engagement with the ball, a set screw 21 may be adjusted as for example by an allen wrench 22, to lock the intermediate ring 11 into a fixed relationship with the outer ring 9.

It will be understood that due to the construction of the elements described above, the present invention permits the socket member 4 and ball member 1 to be implanted separately and then assembled and locked together for relative movement. Prior to assembly, the ends of the U-shaped tool 16 are applied, through the slots 17 and 18 in the outer ring 9, to the depressions 19,20 of the intermediate ring 11, and the tool is then rotated counterclockwise so that the intermediate ring 11 is disposed as shown in FIG. 7. In this condition, the camming grooves are fixed to a position wherein they have forced the pins 14a,14b to their outermost position, thus fully opening the arcuate flanges 7a,7b. The ball 1 is then inserted in the socket 4, whereupon the tool 16 is rotated in the clockwise direction, thereby causing the camming grooves 15a,15b, to force the pins 14a,14b radially inward, thus closing the adjustable retaining mechanism by moving the arcuate flanges inwardly to prevent separation of the ball 1 from the socket 4. At that time, the set screw 21 is adjusted to lock the mechanism in its closed condition.

Figure 8:
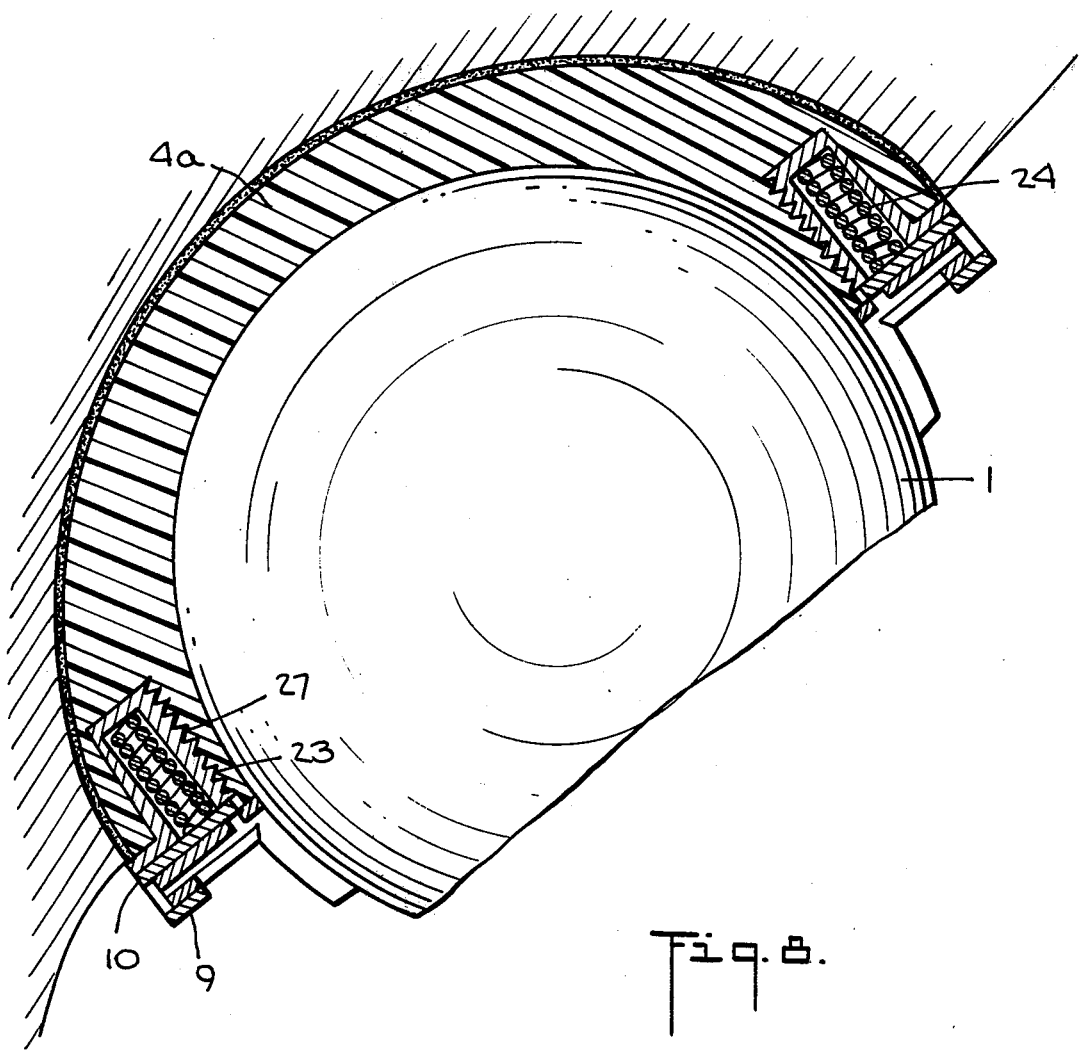
FIG. 8 is an enlarged view showing the disposition of the various elements of the ball and socket assembly, including spring members, in a condition wherein the assembly is not subjected to separating forces.
Figure 9:
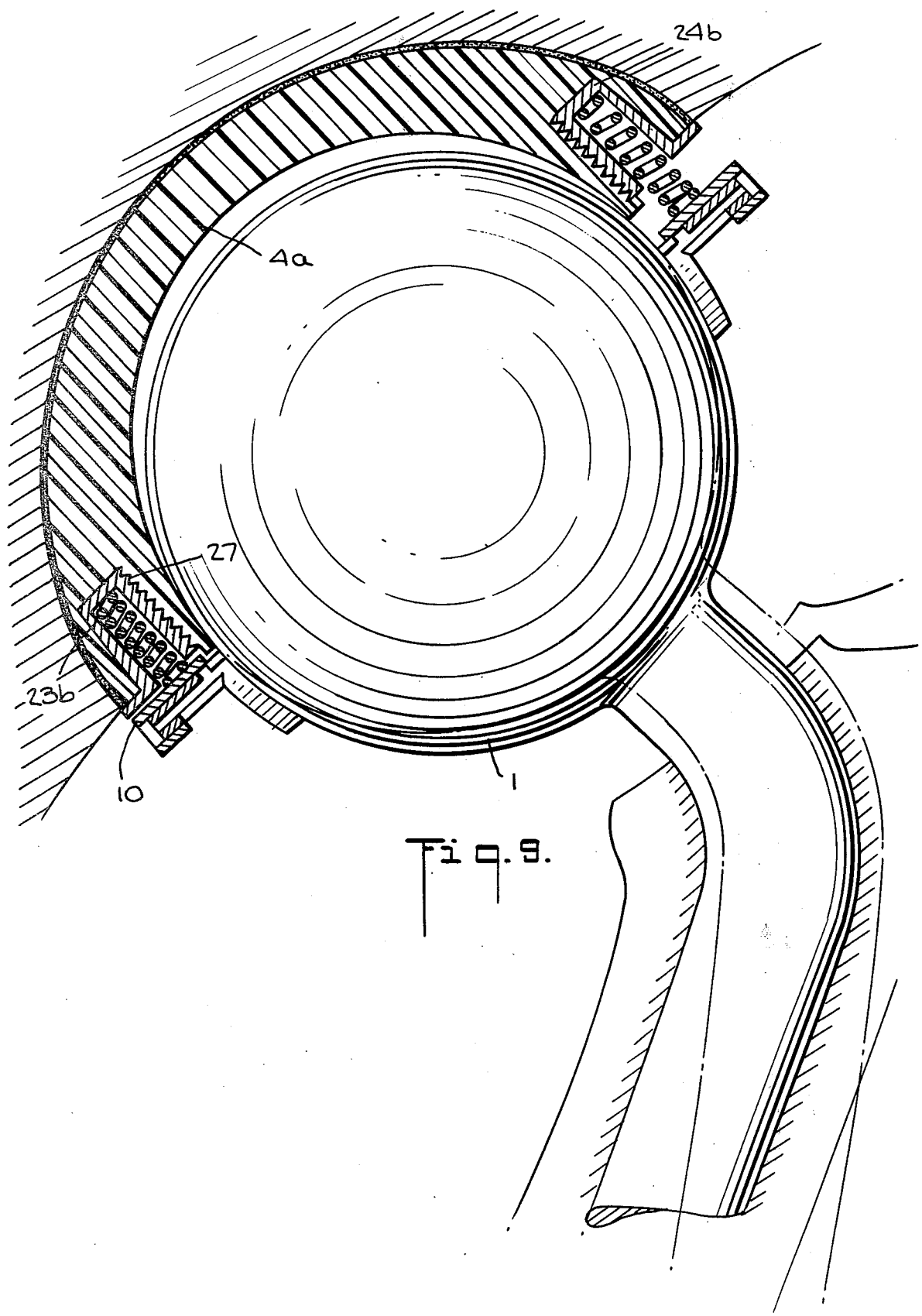
FIG. 9 is a view similar to FIG. 8 showing the absorption of separating forces by one of the spring members.

As shown in detail in the exploded view illustrated in FIG. 4 of the drawings, the assembly of inner and outer rings 9 and 10, having the intermediate ring 11 rotatably held therebetween, is mounted by a plurality of at least two coil springs 23,24 each having one end 23a,24a fixed to the underside of the inner ring 10, wherein such springs are received in recesses 25,26 in an annular housing 27 which is threaded onto a cylindrical element extending outwardly from a cup-shaped element 4a which provides a bearing surface for the ball 1. Thus, the housing 27 and element 4a form a unitary assembly, and as depicted in FIGS. 8 and 9, the opposed ends 23b,24b of the coil springs are fixed to the annular housing member 27 so that a separating force exerted between the ball and socket will cause an extension in at least one of the coil springs 23,24, thus providing a spring-loaded displacement between the inner ring 10 and the housing element 27. It will be appreciated that the selection of an appropriate spring constant for the springs 23 and 24 will alleviate dislodging forces which would otherwise be fully exerted on the cemented joint between the socket element and the acetabular opening 5.

In a modified embodiment of the adjusting mechanism for the arcuate locking flanges 7a,7b, as shown in FIG. 10, the intermediate ring 11' is provided with an arcuately disposed rack type gear 28, while the outer ring 9' is provided with an opening 29 for receiving a pinion-gear wrench 30 for engaging the rack gear 28 to rotate the intermediate ring 11' whereupon sliding movement of the arcuate flanges will occur in the same manner as described above with respect to FIGS. 2-7. The remaining reference numerals set forth in FIG. 10 correspond to the same elements shown in FIG. 4.

It is contemplated that the preferred embodiment of the invention will embody a metallic ball element and that the socket member may comprise a conventional polyethlene material, while the inner surfaces of the arcuate flanges will be coated with a polyethlene material to minimize frictional forces between the flange elements and the ball. An arcuate flange 7c embodying such a polyethlene coating is shown for example in FIG. 11, wherein the element 31 constitutes a friction-reducing bearing element having retaining pins 32 for insertion through openings in the flange 7c.

In summary, the present invention provides separate ball and socket members for being implanted for use as a hip joint prosthesis, wherein the two elements may be locked in place after implantation, and wherein a spring device is provided to absorb forces which would otherwise tend to dislodge the socket member from the acetabular opening.

It is to be understood that the foregoing detailed description is directed toward a preferred embodiment of the invention, and that such invention is not limited to the specific embodiment but encompasses modifications which fall within the claims set forth herein.

What is claimed is:

1. In a hip joint prosthesis of the type having separate ball and socket members for being implanted respectively in femoral and acetabular openings, the improvement wherein the socket member comprises:

means providing a cup-shaped bearing surface for the ball member;

means for retaining the ball member in an assembled position within the socket member; and spring means connected between said cup-shaped bearing surface means and said ball member retaining means for absorbing forces applied in a direction tending to separate the assembled ball and socket members.

2. An improved hip joint prosthesis as set forth in claim 1, wherein said cup-shaped bearing surface means is provided with a plurality of recesses in an outer portion thereof adjacent said ball member retaining means, and wherein said spring means comprises a corresponding plurality of coil springs disposed within said recesses, each said spring being fixedly connected at one end to said retaining means, and fixedly connected at its other end to said bearing surface means.

3. In a hip joint prosthesis of the type having separate ball and socket members for being implanted respectively in femoral and acetabular openings, the improvement wherein the socket member comprises:

means providing a cup-shaped bearing surface for the ball member;

a plurality of flange means having arcuate surfaces for engagement with the ball member, outwardly of said cup-shaped bearing surface, for being disposed to retain the ball member within the cup-shaped bearing surface means;

means mounting said flange means for adjustable movement between an open position wherein the ball member may be freely inserted into or withdrawn from the cup-shaped means and a closed position wherein the ball and socket members are held together as an assembly to permit relative rotational movement therebetween; and locking means for fixing said mounting means in its said closed position.

4. An improved hip joint prosthesis as set forth in claim 3, wherein said mounting means comprises an inner ring disposed at an opening of said cup-shaped bearing surface means, an outer ring fixed to the inner ring, and an intermediate ring disposed for rotational movement between said inner and outer rings, said outer ring having at least one axial opening therethrough for permitting access to said intermediate ring, and having radially extending openings for slidably receiving said flange means therein, said intermediate ring including means responsive to rotational movement thereof for moving said flange means radially between said open and closed positions.

5. An improved hip joint prosthesis as set forth in claim 4, wherein each said flange means includes a depending pin, and said intermediate ring includes semi-circumferential slot means for receiving said pins, and for exerting a camming force on said pins to radially move said flange means in response to said rotational movement of said intermediate ring.

6. An improved hip joint prosthesis as set forth in claim 5, further comprising spring means mounted between said inner ring and said cup-shaped bearing surface means for absorbing forces applied in a direction tending to separate the assembled ball and socket members.

7. An improved hip joint prosthesis as set forth in claim 6, wherein said cup-shaped bearing surface means is provided with a plurality of recesses in an outer portion thereof adjacent said inner ring, and wherein said spring means comprises a corresponding plurality of coil springs disposed within said recesses, each said spring bearing fixedly connected at one end to said inner ring, and fixedly connected at its other end to said bearing surface means.

8. An improved hip joint prosthesis as set forth in claim 3, further comprising spring means connected between said mounting means and said cup-shaped bearing surface means for absorbing forces applied in a direction tending to separate the assembled ball and socket members.

* * * * *